United States Patent
Kenchaiah et al.

(10) Patent No.: US 11,078,212 B2
(45) Date of Patent: Aug. 3, 2021

(54) 2-HYDROCARBYL-3-(DIHYDROXY-FLUORESCEINYL)PHTHALIMIDINE MONOMERS, METHODS OF MANUFACTURE, AND COPOLYMERS DERIVED THEREFROM

(71) Applicant: SABIC GLOBAL TECHNOLOGIES B.V., Bergen Op Zoom (NL)

(72) Inventors: Lohith Kenchaiah, Bangalore (IN); Vijayakumar Venkatesh Sugur, Bangalore (IN); Rashmi R. Deshpande, Bangalore (IN); Hariharan Ramalingam, Bangalore (IN); James Alan Mahood, Evansville, IN (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 241 days.

(21) Appl. No.: 16/428,082

(22) Filed: May 31, 2019

(65) Prior Publication Data
US 2020/0002349 A1 Jan. 2, 2020

(30) Foreign Application Priority Data
Jun. 29, 2018 (EP) .................................... 18181020

(51) Int. Cl.
*C07D 491/107* (2006.01)
*C08G 64/30* (2006.01)

(52) U.S. Cl.
CPC ....... *C07D 491/107* (2013.01); *C08G 64/305* (2013.01)

(58) Field of Classification Search
USPC .............. 528/201; 514/19.2, 19.3, 409, 412; 548/409, 410; 546/12, 15
See application file for complete search history.

(56) References Cited

U.S. PATENT DOCUMENTS

| 3,036,039 | A | 5/1962 | Howe |
| 2016/0060403 | A1 | 3/2016 | Mahood et al. |
| 2017/0276607 | A1* | 9/2017 | Helal ................... G01N 33/582 |

FOREIGN PATENT DOCUMENTS

CN 103159772 A 6/2013

OTHER PUBLICATIONS

Yunfei Zuo,ab Xing Wang*a and Decheng Wu Uniting aggregation-induced emission and stimuli-responsive aggregation-caused quenching, single molecule achieved multicolour luminescence; Journal of Materials Chemistry C., 2019, 7, 14555 (Year: 2019).*
Adamczyk et al., "Synthesis of Novel Spirolactams by Reaction of Fluorescein Methyl Ester With Amines," 2000, 41, 807-809, XP004188496; 4 pages.
Database Reaxys, Database accession No. 628287 (Rx-ID), XP002783722 (D2a); Meyer, Spengler Chemische Be-Richte 1903, 36, 2949-2967 XP055498727 (D2b).
Database Reaxys, Database accession No. 833786 (Rx-ID), XP-002783721, (D1a); & Fischer; Hepp Chemische Berichte, 1893, No. 26, 2236-2238, XP055498735 (D1b).
Database Registry, Database Accession No. 1235007-92-7 (RN), Aug. 5, 2010, XP002783735.
European Search Report; Application No. 18181020.1-1116; dated Aug. 18, 2018; 17 pages.
European Search Report; Application No. 18181020.1-1116; dated Oct. 18, 2018; 15 pages.
Fisher et al., "Ueber Fluoresceinanilid," Chemische Berichte, vol. 26, No. 2, May 1, 1893, pp. 2236-2238, Database Accession No. 833786, XP055498735, DE; 4 pages.
Kang et al., Fluorescent and Colorimetric Detection of Acid Vapors by Using Solid-Supported Rhodamine Hydrazides, (2009) 50, 201-2012, XP025972763; 4 pages.

* cited by examiner

*Primary Examiner* — Terressa Boykin
(74) *Attorney, Agent, or Firm* — Cantor Colburn LLP

(57) ABSTRACT

A purified 2-hydrocarbyl-3-(dihydroxyfluoresceinyl)phthalimidine compound of formula (I):

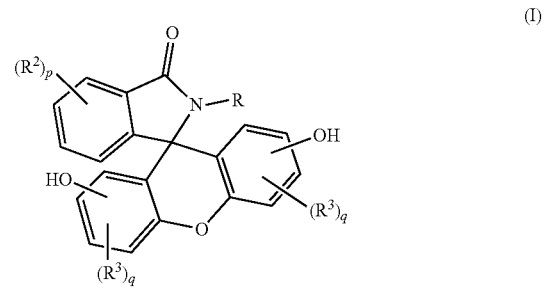

(I)

wherein R is a $C_{1-25}$ hydrocarbyl; each occurrence of $R^2$ and $R^3$ is independently a halogen or a $C_{1-25}$ hydrocarbyl; p is 0 to 4; and each q is independently 0 to 3; and wherein the purified 2-hydrocarbyl-3-(dihydroxyfluoresceinyl)phthalimidine compound of formula (I) has a purity of greater than 99.4%, as determined by high performance liquid chromatography.

20 Claims, No Drawings

2-HYDROCARBYL-3-(DIHYDROXY-FLUORESCEINYL)PHTHALIMIDINE MONOMERS, METHODS OF MANUFACTURE, AND COPOLYMERS DERIVED THEREFROM

CROSS REFERENCE TO RELATED APPLICATIONS

This application claims priority to and the benefit of European Patent Application No. 18181020.1, filed on Jun. 29, 2018, the entire content of which is incorporated by reference herein.

BACKGROUND

This disclosure relates to methods for the manufacture of 2-hydrocarbyl-3-(dihydroxyfluoresceinyl)phthalimidines.

Phenolphthalein derivatives such as 2-phenyl-3,3-bis(4-hydroxyphenyl)phthalimidine (also known as N-phenyl phenolphthalein bisphenol (PPPBP) or 3,3-bis(4-hydroxyphenyl)-2-phenylisoindolin-1-one)) have been used as aromatic dihydroxy compound monomers to prepare polycarbonate resins as well as polyarylate resins. Phenolphthalein derivatives are attractive because they can be used, for example, in polycarbonate copolymers to provide improved properties like higher glass transition temperature ($T_g$), high clarity, and excellent mechanical properties. Currently available methods to synthesize and isolate phenolphthalein derivatives are lengthy and resource intensive. Additionally, purification of dihydroxy phenolphthalein derivatives to reduce impurities such as phenolphthalein and aminophenols can be difficult.

Accordingly, there remains a need for aromatic dihydroxy compound monomers that can be prepared, purified, and incorporated into copolymers to provide high heat stability, a higher $T_g$, and good transparency.

SUMMARY

Provided is a purified 2-hydrocarbyl-3-(dihydroxyfluoresceinyl)phthalimidine compound of formula (I) is provided:

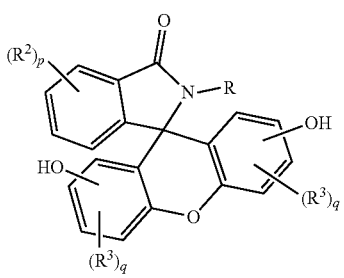

(I)

wherein R is a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl; each occurrence of $R^2$ and $R^3$ is independently halogen or a $C_{1-25}$ hydrocarbyl, preferably a halogen or a $C_{1-6}$ alkyl, more preferably a $C_{1-3}$ alkyl; and p is 0 to 4, preferably 0 or 1, more preferably 0; and each q is independently 0 to 3, preferably 0 or 1, more preferably 0; and wherein the purified 2-hydrocarbyl-3-(dihydroxyfluoresceinyl)phthalimidine compound of formula (I) has a purity of greater than 99.4%, preferably greater than 99.5%, more preferably greater than 99.8%, as determined by high performance liquid chromatography.

Also provided is a method for the manufacture of the purified 2-hydrocarbyl-3-(dihydroxyfluoresceinyl)phthalimidine (I) compound of formula (I), which includes combining a primary amine of formula (II).

(II)

with an aqueous acid to provide a first reaction mixture; adding a fluorescein of formula (III)

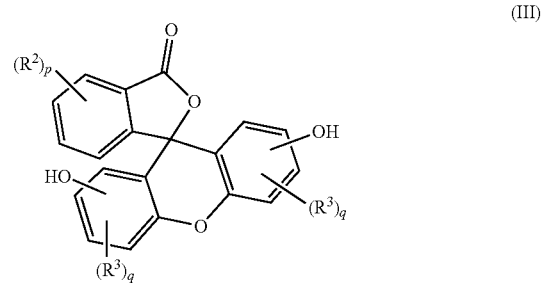

(III)

to the first reaction mixture to provide a second reaction mixture; heating the second reaction mixture under conditions effective to provide a third reaction mixture comprising a crude phthalimidine; combining the crude phthalimidine and an aqueous alkali solution to form an aqueous alkaline mixture; contacting the aqueous alkaline mixture with an adsorbent to provide a semi-purified phthalimidine; and mixing the semi-purified phthalimidine with an alcohol solution to provide the purified 2-hydrocarbyl-3-(dihydroxyfluoresceinyl)phthalimidine compound of formula (I), wherein in formulas (I), (II), and (III), R is a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl; each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; p is 0 to 4, preferably 0 or 1, more preferably 0; and each q is independently 0 to 3, preferably 0 or 1, more preferably 0.

Also provided is a method for the manufacture of a polycarbonate includes polymerizing the purified 2-hydrocarbyl-3-(dihydroxyfluoresceinyl)phthalimidine compound in the presence of a carbonate source under conditions effective to provide the polycarbonate.

In yet another aspect, a polycarbonate is manufactured by the method disclosed herein, wherein the polycarbonate comprises 0 to 0.8 weight percent, preferably 0 to 0.5 weight percent, more preferably 0 to 0.2 weight percent of an impurity derived from the manufacturing of the purified 2-hydrocarbyl-3-(dihydroxyfluoresceinyl)phthalimidine compound.

The disclosure is further illustrated by the following detailed description, examples, and claims.

DETAILED DESCRIPTION

The present disclosure is directed to 2-hydrocarbyl-3-(dihydroxyfluoresceinyl)phthalimidine compounds, purified compounds thereof, the manufacture of the same, and compositions, polymers, and articles derived therefrom. The purified 2-hydrocarbyl-3-(dihydroxyfluoresceinyl)phthalimidine compounds can be used in the manufacture of polycarbonates, polycarbonate copolymers, and other polymers. The purified 2-hydrocarbyl-3-(dihydroxyfluoresceinyl)phthalimidine compound can be prepared in a manner similar to the methods used to prepare 2-phenyl-3,3-bis(hydroxyphenyl)phthalimidine (PPPBP) monomers. Unlike PPPBP, the 2-hydrocarbyl-3-(dihydroxyfluoresceinyl)phthalimidine compound can be prepared as a product that is devoid of or contains a reduced amount of undesirable impurities, for example aminophenol or unreacted phenolphthalein impurities. The purified 2-hydrocarbyl-3-(dihydroxyfluoresceinyl)phthalimidine can be used to provide polymers, such as polycarbonates and copolymers thereof, with properties such as high heat stability, good color stability, excellent clarity, and others.

The purified 2-hydrocarbyl-3-(dihydroxyfluoresceinyl)phthalimidine compound in accordance with this disclosure is of formula (I):

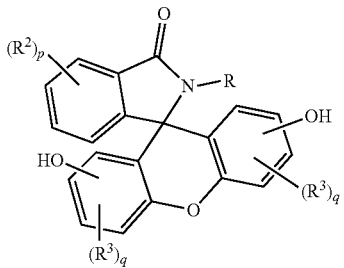

(I)

wherein R is a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl. Each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl, p is 0 to 4, and each q is independently 0 to 3. In some aspects, R is a $C_{1-6}$ alkyl, a phenyl, or a phenyl substituted with up to five $C_{1-6}$ alkyl groups. For example, R can be a $C_{1-3}$ alkyl or a phenyl. In some aspects, $R^2$ and $R^3$ are each independently a halogen or a $C_{1-6}$ alkyl, and p and q are each independently 0 to 3. For example, $R^2$ and $R^3$ each can be independently the same or different $C_{1-3}$ alkyl, and p and q are each independently 0 to 3. In some aspects, p and q are each independently 0 or 1. For example, p can be 1 and $R^2$ can be a $C_{1-3}$ alkyl group. In still other aspects, p and q are each 0.

The purified 2-hydrocarbyl-3-(dihydroxyfluoresceinyl)phthalimidine compound of formula (I) can be of formula (IA)

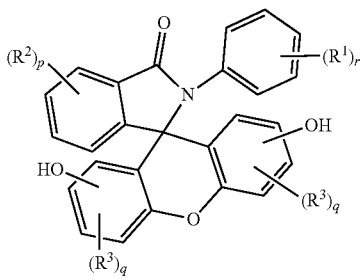

(IA)

wherein each occurrence of $R^1$ is independently a phenyl or a $C_{1-6}$ alkyl; p is 0 to 4, q is 0 to 3, and r is 0 to 5, preferably 0 or 1. Each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; and q are each independently 0 to 3, preferably 0 or 1, more preferably 0. In some aspects, $R^1$ is a $C_{1-3}$ alkyl and r is 0 or 1. In certain aspects, $R^2$ and $R^3$ each can be independently a $C_{1-3}$ alkyl, and p and q are each independently 0 or 1. In some aspects, r is 0. In other aspects, p is 0.

When q is 0 in formulas (I) and (IA), the purified 2-hydrocarbyl-3-(dihydroxyfluoresceinyl)phthalimidine compound of formula (I) can be of formula (IB)

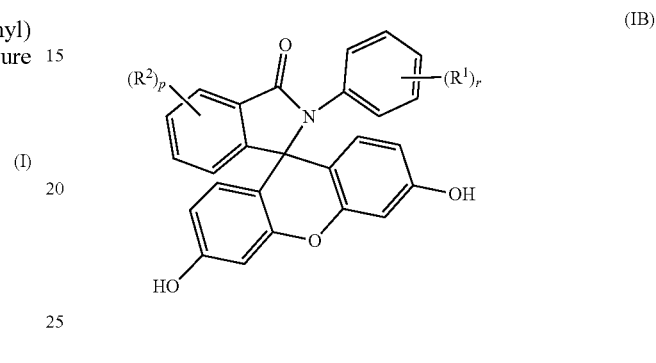

(IB)

wherein each occurrence of $R^1$ is independently a phenyl or a $C_{1-6}$ alkyl, more preferably a $C_{1-3}$ alkyl, and r is 0 or 1. Each occurrence of $R^2$ is independently a halogen or a $C_{1-25}$ hydrocarbyl, preferably a halogen or a $C_{1-6}$ alkyl, more preferably a $C_{1-3}$ alkyl, and p is 0 or 1. In some aspects, $R^1$ is a $C_{1-3}$ alkyl and $R^2$ is a $C_{1-3}$ alkyl, and p and r each are 1. In other aspects, p and r are 0.

When p, q, and r are 0 in formulas (I), (IA), and (IB), the purified 2-hydrocarbyl-3-(dihydroxyfluoresceinyl)phthalimidine compound is of formula (IC)

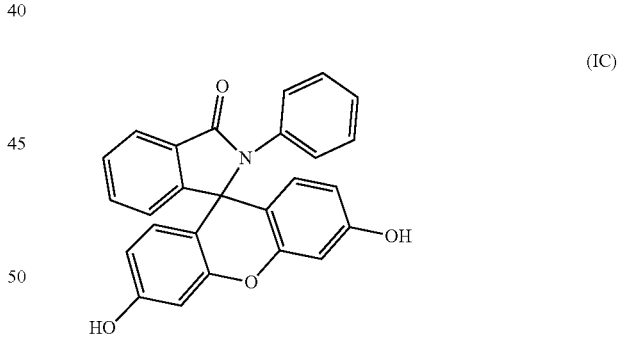

(IC)

The purified 2-hydrocarbyl-3-(dihydroxyfluoresceinyl)phthalimidine compound can be prepared by reaction of a substituted or unsubstituted fluorescein compound and an acid salt of an amine compound. For example, the method for the manufacture of the purified 2-hydrocarbyl-3-(dihydroxyfluoresceinyl)phthalimidine compound of formula (I) can include combining a primary amine of formula (II)

 R—NH$_2$ (II)

with an aqueous acid to form a first reaction mixture, and adding a fluorescein compound of formula (III)

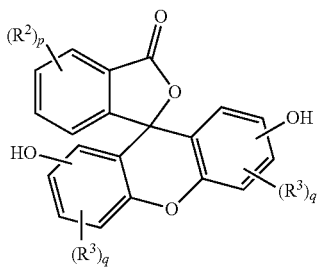

(III)

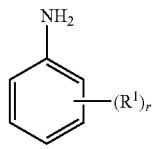

(IIA)

to the first reaction mixture to provide a second reaction mixture. In formula (II), R can be a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl. In formula (III), each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; p can be 0 to 4, preferably 0 or 1, more preferably 0; and each q can independently be 0 to 3, preferably 0 or 1, more preferably 0. In some aspects, at least some water is removed from the first reaction mixture before adding the fluorescein compound.

The acid salt of the primary amine of formula (II) can isolated from the first reaction mixture, and the acid salt of the primary amine can be combined with the fluorescein of formula (III) to provide the second reaction mixture. For example, the acid salt of the primary amine of formula (II) can be isolated by mixing the first reaction mixture with aqueous acid and water, and then filtering the acid salt of the primary amine of formula (II). In some aspects, the precipitated acid salt of the primary amine of formula (II) an be dried, for example continuously dried, to achieve a desired content or amount of water, for example less than 2 weight percent (wt %) of water, based on the weight of the acid salt of the primary amine of formula (II).

Exemplary aqueous acids include, but are not limited to, mineral acids. The mineral acids can be present in a fluid phase, for example, in a gaseous phase or in a liquid phase or in a combination of the gaseous and liquid phases. Non-limiting examples of mineral acids include hydrogen chloride liquid, hydrogen chloride gas, sulfuric acid, nitric acid, a combination thereof, or the like.

The aqueous acid can be present in the first reaction mixture at a concentration of 0.8 to 1.5 molar equivalents of the primary amine of formula (II). For example, the aqueous acid can be present at a concentration of 0.9 to 1.5, or 1 to 1.5, or 0.9 to 1.2 molar equivalents of the primary amine of formula (II). As used herein, the concentration of the aqueous acid in the first reaction mixture refers to the molar equivalents of the aqueous acid that are combined with the primary amine to provide the first reaction mixture.

The primary amine of formula (II) can be present in the second reaction mixture at a concentration of 2 to 5 molar equivalents of the fluorescein of formula (III). For example, the primary amine of formula (II) can be present in the second reaction mixture at a concentration of 2.2 to 4.6, 2.4 to 4, 2.6 to 3.8, or 2.8 to 3.6 molar equivalents of the fluorescein of formula (III). As used herein, the concentration of the primary amine in the second reaction mixture refers to the concentration of the free amine.

The primary amine of formula (II) can be a primary arylamine of formula (IIA)

wherein $R^1$ and r are as described in formula (I). In some aspects, the primary arylamine is aniline or a substituted derivative thereof.

The second reaction mixture, which is formed by combining either the first reaction mixture or the isolated acid salt of the primary amine of formula (II) and the fluorescein of formula (III), can be heated to provide a third reaction mixture including a crude phthalimidine of formula (I). The second reaction mixture can be heated at a suitable temperature and for a suitable time to provide the third reaction mixture comprising the crude phthalimidine. For example, the second reaction mixture can be heated at 100 to 200° C. for 10 to 40 hours, preferably at 120 to 180° C. for 15 to 35 hours.

The third reaction mixture can be combined (e.g., mixed) with an additional amount of aqueous acid to provide the crude phthalimidine. The third reaction mixture can be heated after the addition of the additional aqueous acid, for example at 80 to 150° C. The amount of the additional aqueous acid can be sufficient to convert the remaining primary amine of formula (II) in the third reaction mixture to the corresponding acid salt.

In some aspects, the crude phthalimidine can be isolated from the third reaction mixture and optionally dried. For example, the crude phthalimidine can be isolated by combining (e.g., mixing) the third reaction mixture with the additional amount of aqueous acid and water, and then filtering the crude phthalimidine from the mixture.

The crude phthalimidine can be combined with an aqueous alkali solution to form an aqueous alkaline mixture. The aqueous alkali solution can include an aqueous solution of an alkali metal hydroxide, an alkaline earth metal hydroxide, or a combination thereof. For example, the aqueous alkali solution can include sodium hydroxide.

The aqueous alkali solution can be present at a concentration of 1.5 to 3.0 molar equivalents of the crude phthalimidine. For example, the concentration of the aqueous alkali solution can be 1.5 to 2.5, or 1.75 to 2.75, or 2.0 to 3.0 molar equivalents of the crude phthalimidine.

The aqueous alkaline mixture can be contacted with an adsorbent, for example one or more of activated carbon, silica, alumina, clay, a zeolite, or the like, to remove traces of one or more impurities and to decolorize the mixture, to provide a semi-purified phthalimidine of formula (I). For example, a commercially available activated carbon can be used. Exemplary activated carbons include, but are not limited to, the NORIT series of activated carbon available from Norit Corporation, and those available from E. Merck Company.

In some aspects, the aqueous alkaline mixture can be contacted one or more times with the adsorbent to provide the semi-purified product. In particular aspects, an acid can be combined with the aqueous alkaline mixture after it is contacted with the adsorbent to precipitate a solid product and provide the semi-purified phthalimidine. The acid can be a dilute aqueous solution of a mineral acid such as hydrochloric acid, sulfuric acid, nitric acid, or the like. For example, the semi-purified phthalimidine can be isolated by mixing with the acid, filtering the resulting solid precipitate product, and then washing the semi-purified phthalimidine with deionized water.

The semi-purified phthalimidine can be mixed with a solution including an alcohol and water to form a purified 2-hydrocarbyl-3-(dihydroxyfluoresceinyl)phthalimidine compound of formula (I). Exemplary alcohols include $C_{1-6}$ alcohols such as methanol, ethanol, isopropanol, or the like. For example, the semi-purified product can be mixed with an alcohol solution including methanol and water to form the purified phthalimidine compound.

For example, the semi-purified phthalimidine can be combined with an alcohol solution including an alcohol, for example methanol, and deionized water, and then heated at 50-80° C. to form a solution. An adsorbent, for example a carbonaceous material, can be added to the solution and the resulting mixture is stirred. The adsorbent can then be separated from the solution and an additional amount of deionized water can be added to the solution as needed to provide the purified phthalimidine compound of formula (I).

The method can further include crystallizing the purified 2-hydrocarbyl-3-(dihydroxyfluoresceinyl)phthalimidine compound of formula (I). For example, a slurry including the purified 2-hydrocarbyl-3-(dihydroxyfluoresceinyl) phthalimidine can be concentrated to provide a concentrated slurry (e.g., 60 to 80% solids), followed by separating a wet solid including the purified 2-hydrocarbyl-3-(dihydroxyfluoresceinyl)phthalimidine from the concentrated slurry. Optionally, the wet solid can be re-slurried (e.g., 12 to 30% solids), for example in a solution of methanol and water (90:10 v/v), refluxed at the boiling point of the solvent and cooled for example to −20° C., or 5 to 10° C., to precipitate the purified 2-hydrocarbyl-3-(dihydroxyfluoresceinyl)phthalimidine. The wet solid can then be isolated, for example by crystallization, and the crystals separated from the mother liquor, for example by filtration, and optionally dried to provide the purified 2-hydrocarbyl-3-(dihydroxyfluoresceinyl)phthalimidine.

The purified 2-hydrocarbyl-3-(dihydroxyfluoresceinyl) phthalimidine compound of formula (I) can have a purity of greater than 99.4%, preferably greater than 99.5%, more preferably greater than 99.8%, as determined by high performance liquid chromatography (HPLC).

The purified 2-hydrocarbyl-3-(dihydroxyfluoresceinyl) phthalimidines, including the exemplary purified 2-phenyl-3-(dihydroxyfluoresceinyl)phthalimidine (RPBP), are commercially valuable monomers or comonomers for producing a variety of polymers formed by reactions of the phenolic OH groups of the 2-hydrocarbyl-3-(dihydroxyfluoresceinyl) phthalimidines. Exemplary polymers that can be produced include homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, ester carbonate, and carbonate repeat units, and a polyetherketone. An example of a copolymer including aromatic ester, estercarbonate, and carbonate repeat units is the copolymer produced by the reaction of a hydroxy-terminated polyester, such as the product of reaction of isophthaloyl chloride and terephthaloyl chloride with resorcinol, with phosgene and an aromatic dihydroxy compound, such as bisphenol A.

According to some aspects, polycarbonates having low color properties are synthesized, wherein the polycarbonates include structural units of formula (VI)

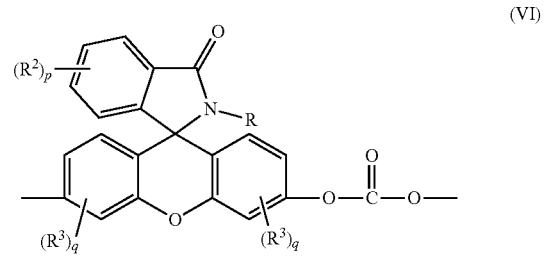

that are derived from the purified 2-hydrocarbyl-3-(dihydroxyfluoresceinyl)phthalimidine compound of formula (I), wherein R, $R^2$, $R^3$, p, and q are as described previously; and the C=O structural units are derived from a C=O donor such as a carbonic acid diester in a melt transesterification process, or phosgene in an interfacial process.

Specific polycarbonates include copolycarbonates having structural units derived from a phthalimidine compound of formula (I) and a dihydroxy compound of the formula HO—$R^1$—OH, in particular of formula (VII)

$$HO-A^1-Y^1-A^2-OH \quad (VII)$$

wherein each of $A^1$ and $A^2$ is a monocyclic divalent aromatic group and $Y^1$ is a single bond or a bridging group having one or more atoms that separate $A^1$ from $A^2$. In an exemplary embodiment, one atom separates $A^1$ from $A^2$. Specifically, each $R^1$ can be derived from a dihydroxy aromatic compound of formula (VIII)

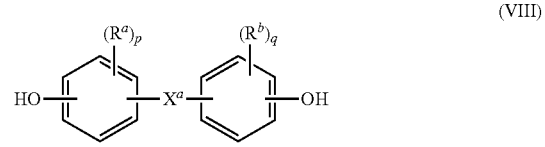

wherein $R^a$ and $R^b$ each represent a halogen or $C_{1-12}$ alkyl group and can be the same or different; and p and q are each independently integers of 0 to 4. $X^a$ represents a single bond or a bridging group connecting the two hydroxy-substituted aromatic groups, where the single bond or the bridging group and the hydroxy substituent of each $C_6$ arylene group are disposed ortho, meta, or para (specifically para) to each other on the $C_6$ arylene group. For example, the bridging group $X^a$ can be —O—, —S—, —S(O)—, —S(O)$_2$—, —C(O)—, or a $C_{1-18}$ organic group. The $C_{1-18}$ organic group can be cyclic or acyclic, aromatic or non-aromatic, and can further include heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic group. In some aspects, p and q is each 1, and $R^a$ and $R^b$ are each a $C_{1-3}$ alkyl group, specifically methyl, disposed meta to the hydroxy group on each arylene group.

The group $X^a$ can be a substituted or unsubstituted $C_{3-18}$ cycloalkylidene, a $C_{1-25}$ alkylidene of formula —C($R^c$) ($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Exemplary groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene. Alternatively, the group $X^a$ can be a $C_{1-18}$ alkylene group, a $C_{3-18}$ cycloalkylene group, a fused $C_{6-18}$ cycloalkylene group, or a group of the formula —$B^1$—W—$B^2$— wherein $B^1$ and $B^2$ are the same or different $C_{1-6}$ alkylene group and W is a $C_{3-12}$ cycloalkylidene group or a $C_{6-16}$ arylene group.

Other exemplary aromatic dihydroxy compounds of the formula HO—$R^1$—OH include compounds of formula (IX)

(IX)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. For example, the halogen can be bromine.

Exemplary aromatic dihydroxy compounds include 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl) propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations thereof.

The aromatic dihydroxy compound can be a bisphenol, such as 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, 1,1-bis(4-hydroxy-3-methylphenyl)cyclohexane (DMBPC), or a combination thereof. For example, the polycarbonate can be a linear homopolymer derived from BPA, wherein $A^1$ and $A^2$ are p-phenylene and $Y^1$ is isopropylidene.

Exemplary carbonic acid diesters in the formation of the polycarbonates in a melt transesterification process can be of formula (X)

$$(ZO)_2C=O \quad (X)$$

wherein each Z is independently an unsubstituted or substituted $C_{1-12}$ alkyl radical, or an unsubstituted or substituted $C_{6-22}$ aryl radical. Examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, or a combination thereof. Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate, or a combination thereof. Exemplary ester-substituted diaryl carbonates include bis(methylsalicyl)carbonate (CAS Registry No. 82091-12-1) (also known as BMSC or bis(o-methoxycarbonylphenyl)carbonate), bis(ethyl salicyl)carbonate, bis(propyl salicyl) carbonate, bis(butylsalicyl) carbonate, bis(benzyl salicyl)carbonate, bis(methyl 4-chlorosalicyl)carbonate, or the like.

The melt transesterification process can be carried out by combining a catalyst, the carbonic acid diester of formula (X), the phthalimidine compound of formula (I), and optionally a dihydroxy comonomer; and mixing the reaction mixture under reactive conditions for a time period effective to produce the polycarbonate product. Exemplary melt transesterification catalysts include alkali metal compounds, alkaline earth metal compounds, tetraorganoammonium compounds, tetraorganophosphonium compounds, or a combination thereof. Example of alkali metal compounds or alkaline earth metal compounds include sodium hydroxide, potassium hydroxide, calcium hydroxide, magnesium hydroxide, sodium bicarbonate, potassium bicarbonate, sodium carbonate, potassium carbonate, lithium carbonate, sodium acetate, potassium acetate, sodium stearate, potassium stearate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, or the like, or a combination thereof. Exemplary tetraorganoammonium compounds and tetraorganophosphonium compounds include tetramethylammonium hydroxide, tetrabutylammonium hydroxide, tetraethylphosphonium hydroxide, tetrabutylphosphonium acetate, tetrabutylphosphonium hydroxide, or the like, or a combination thereof. For example, the catalyst can be a combination of an alkali metal salt or alkaline earth metal salt with at least one quaternary ammonium compound, at least one quaternary phosphonium compound, or a combination thereof. For example, the catalyst can include sodium hydroxide and tetrabutylphosphonium acetate or tetramethylammonium hydroxide. The catalyst can include the salt of a non-volatile inorganic acid, for example alkali metal salts of phosphites; alkaline earth metal salts of phosphites; alkali metal salts of phosphates; and alkaline earth metal salts of phosphates, including $NaH_2PO_3$, $NaH_2PO_4$, $Na_2H_2PO_3$, $KH_2PO_4$, $CsH_2PO_4$, $Cs_2H_2PO_4$, or the like, or a combination thereof. In some aspects, the transesterification catalyst includes both the salt of a non-volatile acid and a basic co-catalyst such as an alkali metal hydroxide. For example, a combination of $NaH_2PO_4$ and sodium hydroxide as the transesterification catalyst.

The catalysts can be used as combinations of two or more substances. Moreover, the catalyst can be added in a variety of forms. For example, the catalyst can be added as a solid powder, or dissolved in a solvent, for example, in water, alcohol, or a combination thereof. The total amount of catalyst can be $1 \times 10^{-7}$ to $2 \times 10^{-3}$ moles, and in other embodiments, $1 \times 10^{-6}$ to $4 \times 10^{-4}$ moles, for each mole of the combination of, for example, the purified RPBP and the aromatic dihydroxy comonomer.

The polymerization reaction can be monitored by measuring the melt viscosity or the weight average molecular weight of the reaction mixture using techniques known in the art such as gel permeation chromatography. These properties can be measured by taking discreet samples or can be measured on-line. After the desired melt viscosity or molecular weight is reached, the final polycarbonate product can be isolated from the reactor in a solid or molten form. The method of making polycarbonates can be a batch or a continuous process.

The melt-polymerized polycarbonate can be prepared in an extruder in the presence of one or more catalysts. The reactants for the polymerization reaction can be fed to the extruder in powder or molten form. For example, the reactants can be dry blended prior to addition to the extruder. The extruder can be equipped with a pressure reducing device (e.g., vents) that serve to remove the activated phenol byproduct and thus drive the polymerization reaction toward completion. The molecular weight of the polycarbonate product can be manipulated by controlling, among other factors, the feed rate of the reactants, the type of extruder, the extruder screw design, and configuration, the residence time in the extruder, the reaction temperature, and the pressure reducing techniques present on the extruder. The molecular weight of the polycarbonate product can also depend upon the structures of the reactants and the catalyst employed.

Alternatively, the polycarbonates can be prepared by an interfacial polymerization process. Although the reaction conditions for interfacial polymerization can vary, an exemplary process involves dissolving or dispersing a dihydric phenol reactant in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., about 8-about 12. Exemplary water immiscible solvents include methylene chloride, 1,2-dichloroethane, chlorobenzene, toluene, and the like.

Exemplary carbonate precursors for interfacial polymerization include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. For example, phosgene can be the carbonate precursor.

Phase transfer catalysts for interfacial polymerization include tetraorganoammonium and tetraorganophosphonium compounds of the formula $(R_3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, Br$^-$, a $C_{1-8}$ alkoxy group or a $C_{6-18}$ aryloxy group. An effective amount of a phase transfer catalyst can be about 0.1 to about 10 wt % based on the weight of bisphenol in the phosgenation mixture. For example, the amount of phase transfer catalyst can be 0.5 to 2 wt %, based on the weight of bisphenol in the phosgenation mixture.

Any polycarbonate end group can be used, provided that such end groups do not significantly adversely affect desired properties of the compositions. Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate. Exemplary chain stoppers include certain mono-phenolic compounds, mono-carboxylic acid chlorides, or mono-chloroformates.

The interfacial method described above can be adapted to produce polycarbonates through the intermediate formation of 2-hydrocarbyl-3-(dihydroxyfluoresceinyl)phthalimidine bischloroformate, via the bischloroformate polymerization method. The method includes reacting a 2-hydrocarbyl-3-(dihydroxyfluoresceinyl)phthalimidine with phosgene in an organic solvent, and then reacting the bischloroformate either with a 2-hydrocarbyl-3-(dihydroxyfluoresceinyl)phthalimidine, or an aromatic dihydroxy compound in the presence of an acid acceptor and an aqueous base to form the polycarbonate. The interfacial polymerization method and the bischloroformate polymerization method can be carried in a batch or a continuous mode using one or more reactor systems. To carry out the process in a continuous mode, one or more continuous reactors, such as for example, a tubular reactor can be used. The continuous method can include introducing into a tubular reactor system phosgene, a solvent (e.g., methylene chloride), a bisphenol, an aqueous base, and optionally a catalyst (e.g., a trialkylamine) to form a flowing reaction mixture. The flowing mixture can be passed through the tubular reactor system until substantially all of the phosgene has been consumed. The resulting mixture can be treated with a combination of an aqueous base, an endcapping agent, optionally a solvent, and a catalyst. The endcapped polycarbonate thus formed can be continuously removed from the tubular reactor system.

The processes disclosed herein can advantageously be used to prepare, for example, RPBP homopolycarbonate and copolycarbonates having a weight average molecular weight ($M_w$) of 3,000 to 150,000 Dalton (Da) and a glass transition temperature ($T_g$) of 80 to 300° C. The number average molecular weight ($M_n$) of the homopolycarbonate and copolycarbonates can be from 1,500 to 75,000 Da.

The glass transition temperature can be determined, for example, by differential scanning calorimetry (DSC). Glass transition temperatures ($T_g$) can be measured using thermal scans in a range from 30 to 250° C. under a nitrogen atmosphere with a heating rate of 10 to 20° C./min.

The molecular weight can be determined, for example, by gel permeation chromatography (GPC) using polystyrene standards.

Polymers include structural units derived from the purified phthalimidines, in particular RPBP, can be used to manufacture polymer blends including units derived from the purified phthalimidine and at least one other thermoplastic polymer. Exemplary thermoplastic polymers include vinyl polymers, (meth)acrylic polymers, polyacrylonitrile, polystyrenes, polyolefins, polyesters, polyurethanes, polyamides, polysulfones, polyimides, polyetherimides, poly(phenylene ethers), poly(phenylene sulfides), poly(ether ketones), poly(ether ether ketones), acrylonitrile-butadiene-styrene (ABS) polymers, poly(ether sulfones), poly(alkenyl aromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, poly(vinylidene fluoride), poly(vinylidene chloride), tetrafluoroethylene, polycarbonate-polyorganosiloxane block copolymers, copolymers comprising aromatic ester, estercarbonate, and carbonate repeat units, or a combination thereof.

The polymers and polymer blends described hereinabove are valuable for producing articles. Also provide herein is an article including a polymer having structural units derived from the purified 2-hydrocarbyl-3-(dihydroxyfluoresceinyl) phthalimidine of formula (I).

Polymers, particularly polycarbonate homopolymers and copolymers comprising structural units derived from the high purity 2-hydrocarbyl-3-(dihydroxyfluoresceinyl) phthalimidine in general, and RPBP in particular, exhibit reduced visual coloration. As such, these polycarbonate polymers are useful for producing articles having particular properties, such as lower visual color, among others. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85%.

Polycarbonate homopolymers and copolymers comprising structural units derived from the high purity 2-hydrocarbyl-3-(dihydroxyfluoresceinyl)phthalimidine can have a yellowness index (YI) of less than 10, preferably less than 5, more preferably less than 2, even more preferably less than 0.5 as measured on a 3 millimeter thick plaque in accordance with ASTM D1925.

The polycarbonate polymers are useful for producing articles having a number of useful properties, such as a low residual color. The articles also exhibit excellent heat aging. Thus, extruded articles have low color values (as measured by yellowness index, YI) even after heat aging, such as, for example, a YI of less than 10, preferably less than 5, more preferably less than 2 after heat aging in air at 155 to 160° C. for 500 hours, or a YI of less than 5, preferably less than 2, more preferably less than 0.5 after heat aging in air at 120° C. for 500 hours.

Also provided are thermoplastic compositions including the polycarbonate polymers having structural units derived from the purified 2-hydrocarbyl-3-(dihydroxyfluoresceinyl) phthalimidine. The thermoplastic compositions can include various additives ordinarily incorporated into polymer compositions of this type, with the proviso that the additive(s) are selected so as to not significantly adversely affect the desired properties of the thermoplastic composition, in particular low color. Such additives can be mixed at a suitable time during the mixing of the components for forming the composition. The additive can be soluble or non-soluble in polycarbonate. The additive composition can include an impact modifier, flow modifier, filler (e.g., a particulate polytetrafluoroethylene (PTFE), glass, carbon, mineral, or metal), reinforcing agent (e.g., glass fibers), antioxidant, heat stabilizer, light stabilizer, ultraviolet (UV) light stabilizer, UV absorbing additive, plasticizer, lubricant, release agent (such as a mold release agent), antistatic agent, anti-fog agent, antimicrobial agent, colorant (e.g., a dye or pigment), surface effect additive, radiation stabilizer, flame retardant, anti-drip agent (e.g., a PTFE-encapsulated styrene-acrylonitrile copolymer (TSAN)), or a combination thereof. For example, a combination of a heat stabilizer, mold release agent, and ultraviolet light stabilizer can be used. In general, the additives are used in the amounts generally known to be effective. For example, the total amount of the additive composition (other than any impact modifier, filler, or reinforcing agent) can be 0.001 to 10.0 wt %, or 0.01 to 5 wt %, each based on the total weight of the polymer in the composition.

The methods described herein are further illustrated by the following non-limiting examples.

EXAMPLES

The components in Table 1 were used in the examples. Unless specifically indicated otherwise, the amount of each component is in weight percent (wt %) in the following examples, based on the total weight of the composition.

TABLE 1

| Component | CAS number | Source |
| --- | --- | --- |
| Fluorescein | 2321-07-5 | Sigma-Aldrich |
| Aniline | 62-53-3 | Merck |
| HCl | 7647-01-0 | Vetec |
| NaOH | 1310-73-2 | SD Fine |
| Activated Charcoal | 7440-44-0 | SD fine |
| Diatomaceous Earth | 61790-53-2 | SD Fine |

High performance liquid chromatography (HPLC) analysis was generally carried out by using a solution of about 50 milligrams of the sample dissolved in about 10 milliliters of methanol. The HPLC instrument was equipped with a C18 (reverse phase) column maintained at a temperature of 40° C., and an ultraviolet (UV) detector capable of detecting components at a wavelength of 230 nanometers (nm). A solvent mixture of methanol and water of varying relative proportions was used. The flow rate was maintained at 1 milliliter per minute. The purity was evaluated by area normalization.

Example 1

140 g of aniline and 40 ml of 33% of HCl (33 wt % in water) were combined in a four-neck round bottom flask fitted with an overhead condenser, nitrogen inlet, and overhead stirrer. The reaction mixture was stirred for 1 hour to provide an aniline hydrochloride salt. 100 g of fluorescein was then added to the reaction mixture and the resulting mixture was heated at 170° C. for 30 hours. The progress of the reaction was monitored by thin layer chromatography (TLC) using silica plates in a 1:1 solution of ethyl acetate and hexanes. After completion of the reaction, the temperature was reduced to 120° C. and 150 ml of HCl (33 wt % in water) was added to thereto to convert the remaining aniline to the corresponding hydrochloride salt. 400 ml of deionized water was subsequently added, and the resulting mixture was stirred for one hour. The solids were filtered, collected, and dried at 120° C. to provide a crude phthalimidine product. The purity of the crude product was 81.7%, as determined by HPLC.

Example 2

50 g of the crude phthalimidine product from Example 1 and 500 ml of an aqueous solution of NaOH (10 wt % in water) were combined in three-neck round bottom flask fitted with a nitrogen inlet and an overhead stirrer. The reaction mixture was stirred for one hour and then filtered to remove the insoluble components. The filtrate was collected and combined with 10 wt % of activated charcoal (based on the weight of the crude product), stirred for 2 hours at 25° C., and then filtered over diatomaceous earth. The treatment with activated charcoal was repeated a second time, and the resulting filtrate was precipitated by the addition of HCl (dilute). The resulting solid was isolated by filtration and washed with deionized water to remove residual aniline chloride. The purity of the semi-purified phthalimidine product was 99.3%, as determined by HPLC.

Example 3

The semi-purified phthalimidine product was combined with a mixture of methanol and water (90:10 vol/vol) and dissolved to form a solution (20 wt % product) by heating at 60° C. Activated charcoal (10 wt % based on the weight of the crude product) was added to the solution and the resulting mixture was stirred for one hour at 60° C. The mixture was filtered to separate the activated charcoal and then diluted with deionized water (10 parts by volume based on the total volume of the methanol and water mixture). The mixture was stirred for 30 minutes at 25° C. The purified phthalimidine product was then isolated by filtration. The purity of the purified phthalimidine product was 99.8%, as determined by HPLC.

The purified phthalimidine product was further characterized by liquid chromatography-mass spectrometry (LC-MS) and proton nuclear magnetic resonance ($^1$H-NMR) spectroscopy. LC-MS: m/z=406 Dalton [M-H]. $^1$H NMR: (DMSO-$d_6$) δ=9.90 ppm (s, 2H), 7.29 ppm (d, 1H), 7.60 ppm (m, 2H), 7.15 ppm (m, 4H), 6.64 ppm (m, 4H), and 6.55 ppm (m, 4H).

Table 2 summarizes the purity for Examples 1-3 as determined by HPLC.

TABLE 2

| Sample | Purity |
| --- | --- |
| Example 1 | 81.7% |
| Example 2 | 99.3% |
| Example 3 | 99.8% |

The disclosure is further illustrated by the following non-limiting Aspects.

Aspect 1: A purified 2-hydrocarbyl-3-(dihydroxyfluoresceinyl)phthalimidine compound of formula (I)

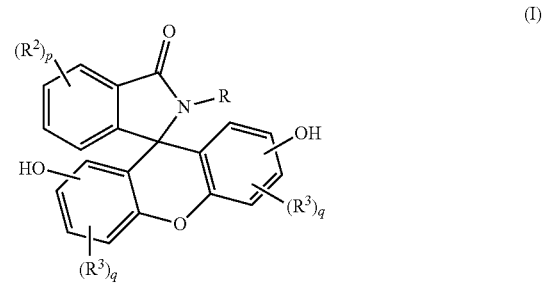

wherein R is a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl; each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; p is 0 to 4, preferably 0 or 1, more preferably 0; and each q is independently 0 to 3, preferably 0 or 1, more preferably 0; and wherein the purified 2-hydrocarbyl-3-(dihydroxyfluoresceinyl)phthalimidine compound of formula (I) has a purity of greater than 99.4%, preferably greater than 99.5%, more preferably greater than 99.8%, as determined by high performance liquid chromatography.

Aspect 2: The compound of Aspect 1, wherein the compound is a purified 2-aryl-3-(dihydroxyfluoresceinyl)phthalimidine compound of formula (IA)

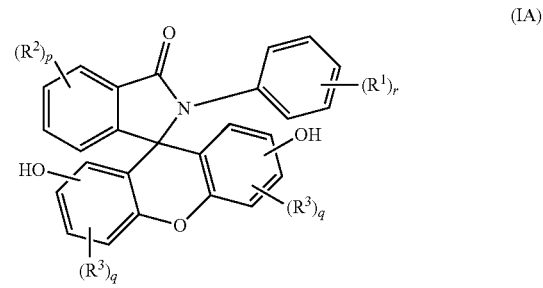

wherein each occurrence of $R^1$ is independently a phenyl or a $C_{1-6}$ alkyl, preferably a phenyl or a $C_{1-3}$ alkyl; each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; p is 0 to 4, preferably 0 or 1, more preferably 0; and each q is independently 0 to 3, preferably 0 or 1, more preferably 0; and wherein the purified 2-aryl-3-(dihydroxyfluoresceinyl)phthalimidine compound of formula (IA) has a purity of greater than 99.4%, preferably greater than 99.5%, more preferably greater than 99.8%, as determined by high performance liquid chromatography.

Aspect 3: The compound of Aspect 1, wherein the compound is a purified 2-aryl-3-(dihydroxyfluoresceinyl)phthalimidine of formula (IB)

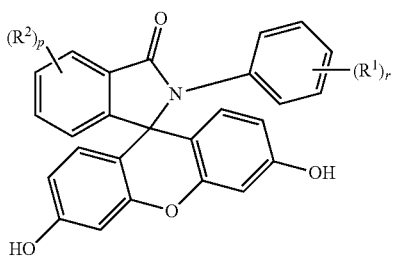

(IB)

wherein each occurrence of $R^1$ is independently a phenyl or a $C_{1-6}$ alkyl, more preferably a phenyl or a $C_{1-3}$ alkyl; each occurrence of $R^2$ is independently a halogen or a $C_{1-25}$ hydrocarbyl, preferably a halogen or a $C_{1-6}$ alkyl, more preferably a $C_{1-3}$ alkyl; p is 0 to 4, preferably 0 or 1, more preferably 0; and each q is independently 0 to 3, preferably 0 or 1, more preferably 0; and wherein the purified compound of formula (IA) has a purity of greater than 99.4%, preferably greater than 99.5%, more preferably greater than 99.8%, as determined by high performance liquid chromatography; preferably wherein each of p and r is zero, and the compound is a purified 2-phenyl-3-(dihydroxyfluoresceinyl) phthalimidine compound of formula (IC) as provided herein, wherein the purified compound of formula (IC) has a purity of greater than 99.4%, preferably greater than 99.5%, more preferably greater than 99.8%, as determined by HPLC.

Aspect 4: The compound of aspect 1, wherein the compound is a purified 2-phenyl-3-(dihydroxyfluoresceinyl) phthalimidine compound of formula (IC)

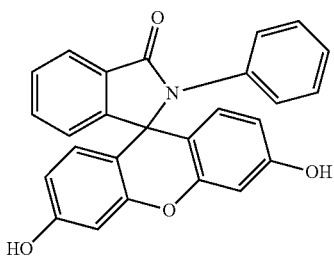

(IC)

wherein the purified 2-phenyl-3-(dihydroxyfluoresceinyl) phthalimidine compound of formula (IC) has a purity of greater than 99.4%, as determined by high performance liquid chromatography.

Aspect 5: A method for the manufacture of the purified 2-hydrocarbyl-3-(dihydroxyfluoresceinyl)phthalimidine (I) compound of Aspect 1, the method comprising: combining a primary amine of formula (II) as provided herein with an aqueous acid to provide a first reaction mixture; adding a fluorescein of formula (III) as provided herein to the first reaction mixture to provide a second reaction mixture; heating the second reaction mixture under conditions effective to provide a third reaction mixture comprising a crude phthalimidine; combining the crude phthalimidine and an aqueous alkali solution to form an aqueous alkaline mixture; contacting the aqueous alkaline mixture with an adsorbent to provide a semi-purified phthalimidine; and mixing the semi-purified phthalimidine with an alcohol solution to provide the purified 2-hydrocarbyl-3-(dihydroxyfluoresceinyl) phthalimidine compound of formula (I), wherein in formulas (I), (II), and (III), R is a $C_{1-25}$ hydrocarbyl, preferably a $C_{1-6}$ alkyl, a phenyl, or a phenyl substituted with up to five $C_{1-6}$ alkyl groups, more preferably a $C_{1-3}$ alkyl or a phenyl; each occurrence of $R^2$ and $R^3$ is independently a halogen or a $C_{1-25}$ hydrocarbyl, preferably a halogen or a $C_{1-6}$ alkyl, more preferably a $C_{1-3}$ alkyl; and p and q are each independently 0 to 4, preferably 0 or 1, more preferably 0.

Aspect 6: The method of Aspect 5, further comprising one or more of mixing the third reaction mixture with aqueous acid to provide the crude phthalimidine; or contacting the aqueous alkaline mixture with the adsorbent, then mixing with an acid to provide the semi-purified phthalimidine.

Aspect 7: The method of Aspect 5 or Aspect 6, further comprising mixing the semi-purified phthalimidine with an alcohol solution and heating to form a solution comprising the semi-purified phthalimide; and contacting the solution with an adsorbent, then mixing with deionized water to provide the purified 2-hydrocarbyl-3-(dihydroxyfluoresceinyl)phthalimidine compound of formula (I).

Aspect 8: The method of any one or more of Aspects 5 to 7, further comprising one or more of isolating the crude phthalimidine from the third reaction mixture, then drying the crude phthalimidine, preferably wherein the isolating comprises mixing the third reaction mixture with aqueous acid and water, then filtering the crude phthalimidine; or isolating the semi-purified phthalimidine, then washing the semi-purified phthalimidine, preferably wherein the isolating comprises mixing with an acid, then filtering the semi-purified phthalimidine.

Aspect 8a: The method of Aspect 8, wherein the isolating of the crude phthalimidine comprises: mixing the third reaction mixture with aqueous acid and water to provide the crude phthalimidine, and filtering the crude phthalimidine.

Aspect 8b: The method of Aspect 8, wherein the isolating of the semi-purified phthalimidine comprises: contacting the aqueous alkaline mixture and the adsorbent with an acid to provide the semi-purified phthalimidine, and filtering the semi-purified phthalimidine.

Aspect 9: The method of any one or more of Aspects 5 to 8, wherein the heating the second reaction mixture is at 100 to 200° C., preferably at 120 to 180° C.

Aspect 10: The method of any one or more of Aspects 5 to 9, wherein the heating the second reaction mixture is for 10 to 40 hours, preferably 15 to 35 hours.

Aspect 10a: The method of Aspect 10, wherein the heating of the second reaction mixture is at 120 to 180° C. for 15 to 35 hours.

Aspect 11: The method of any one or more of Aspects 5 to 10, wherein the primary amine is a primary arylamine of formula (IIA) as provided herein, wherein each occurrence of $R^1$ is independently phenyl or $C_{1-6}$ alkyl, preferably a $C_{1-3}$ alkyl; and r is 0 or 1, preferably 0.

Aspect 12: The method of any one or more of Aspects 5 to 11, wherein the primary amine is aniline.

Aspect 13: The method of any one or more of Aspects 5 to 12, wherein the aqueous acid comprises an aqueous solution of a mineral acid, preferably hydrochloric acid, and the aqueous alkali solution comprises an aqueous solution of an alkali metal hydroxide or an alkaline earth metal hydroxide, preferably sodium hydroxide.

Aspect 14: The method of any one or more of Aspects 5 to 13, wherein the primary amine of formula (II) is present in the second reaction mixture at a concentration of 2 to 5, preferably 2 to 4 molar equivalents of the fluorescein of formula (III), and the aqueous acid is present in the first reaction mixture at a concentration of 0.8 to 1.5, preferably 0.9 to 1.2 molar equivalents of the primary amine of formula (II).

Aspect 15: The method of any one or more of Aspects 5 to 14, wherein the purity of the crude phthalimidine is less than 99%, the purity of the semi-purified phthalimidine is less than 99.5%, and the purity of the purified 2-hydrocarbyl-3-(dihydroxyfluoresceinyl)phthalimidine compound is 99.5% or greater.

Aspect 16: A method for the manufacture of a polycarbonate, the method comprising polymerizing the purified 2-hydrocarbyl-3-(dihydroxyfluoresceinyl)phthalimidine compound of any one or more of Aspects 1 to 4 or manufactured by the method of any one or more of Aspects 5 to 16 in the presence of a carbonate source under conditions effective to provide the polycarbonate.

Aspect 16a: The method of Aspect 16, wherein the polycarbonate comprises 0 to 0.8 weight percent of an impurity derived from the manufacturing of the purified 2-hydrocarbyl-3-(dihydroxyfluoresceinyl)phthalimidine compound.

Aspect 17: A polycarbonate manufactured by the method of Aspect 16, wherein the polycarbonate comprises 0 to 0.8 weight percent, preferably 0 to 0.5 weight percent, more preferably 0 to 0.2 weight percent of an impurity derived from the manufacturing of the purified 2-hydrocarbyl-3-(dihydroxyfluoresceinyl)phthalimidine compound.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt %, or, more specifically, 5-20 wt %", is inclusive of the endpoints and all intermediate values of the ranges of "5 wt % to 25 wt %," etc.). "Combinations" is inclusive of blends, mixtures, alloys, reaction products, and the like. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some aspects", "an aspect", and so forth, means that a particular element described in connection with the aspect is included in at least one aspect described herein, and may or may not be present in other aspects. In addition, it is to be understood that the described elements can be combined in any suitable manner in the various aspects. As used herein, "a combination thereof" is an open term that includes any combination of the listed components and can further include other components that are similar.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

"Hydrocarbyl" as used herein refers to a monovalent moiety formed by removing a hydrogen atom from a hydrocarbon. Representative hydrocarbyls are alkyl groups having 1 to 25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; arylalkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl).

The prefix "halo" means a group or compound including one more of a fluoro, chloro, bromo, or iodo substituent. A combination of different halo groups (e.g., bromo and fluoro), or only chloro groups can be present. "Halogen" or "halogen atom" as used herein refers to a fluorine, chlorine, bromine, or iodine atom.

The prefix "hetero" means that the compound or group includes at least one ring member that is a heteroatom (e.g., 1, 2, or 3 heteroatom(s)), wherein the heteroatom(s) is each independently N, O, S, Si, or P.

"Substituted" means that the compound, group, or atom is substituted with at least one (e.g., 1, 2, 3, or 4) substituents instead of hydrogen, where each substituent is independently nitro (—NO$_2$), cyano (—CN), hydroxy (—OH), halogen, thiol (—SH), thiocyano (—SCN), C$_{1-6}$ alkyl, C$_{2-6}$ alkenyl, C$_{2-6}$ alkynyl, C$_{1-6}$ haloalkyl, C$_{1-9}$ alkoxy, C$_{1-6}$ haloalkoxy, C$_{3-12}$ cycloalkyl, C$_{5-18}$ cycloalkenyl, C$_{6-12}$ aryl, C$_{7-13}$ arylalkylene (e.g., benzyl), C$_{7-12}$ alkylarylene (e.g., toluyl), C$_{4-12}$ heterocycloalkyl, C$_{3-12}$ heteroaryl, C$_{1-6}$ alkyl sulfonyl (—S(=O)$_2$-alkyl), C$_{6-12}$ arylsulfonyl (—S(=O)$_2$-aryl), or tosyl (CH$_3$C$_6$H$_4$SO$_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the compound or group, excluding those of any substituents. For example, a group having the formula —CH$_2$CH$_2$CN is a C$_2$ alkyl group substituted with a cyano substituent.

While particular aspects have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A purified 2-hydrocarbyl-3-(dihydroxyfluoresceinyl)phthalimidine compound of formula (I)

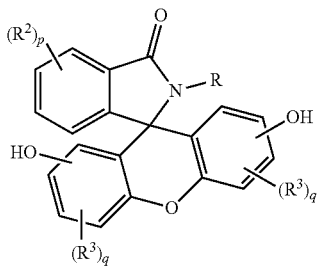

(I)

wherein
R is a $C_{1-25}$ hydrocarbyl;
each occurrence of $R^2$ and $R^3$ is independently a halogen or a $C_{1-25}$ hydrocarbyl;
p is 0 to 4; and
each q is independently 0 to 3, and
wherein the purified 2-hydrocarbyl-3-(dihydroxyfluoresceinyl)phthalimidine compound of formula (I) has a purity of greater than 99.4%, as determined by high performance liquid chromatography.

2. The compound of claim 1, wherein the compound is a purified 2-aryl-3-(dihydroxyfluoresceinyl)phthalimidine compound of formula (IA)

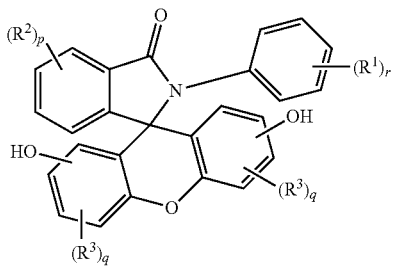

(IA)

wherein
each occurrence of $R^1$ is independently a phenyl or a $C_{1-6}$ alkyl;
each occurrence of $R^2$ and $R^3$ is independently a halogen or a $C_{1-25}$ hydrocarbyl;
p is 0 to 4;
each q is independently 0 to 3; and
r is 0 to 5, and
wherein the purified 2-aryl-3-(dihydroxyfluoresceinyl)phthalimidine compound of formula (IA) has a purity of greater than 99.4%, as determined by high performance liquid chromatography.

3. The compound of claim 1, wherein the compound is a purified 2-aryl-3-(dihydroxyfluoresceinyl)phthalimidine compound of formula (IB)

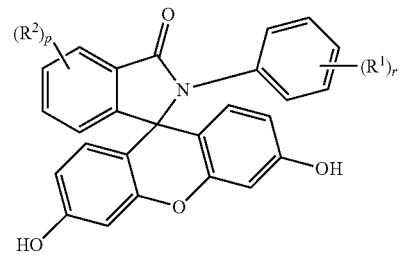

(IB)

wherein
each occurrence of $R^1$ is independently a phenyl or a $C_{1-6}$ alkyl;
each occurrence of $R^2$ is independently a halogen or a $C_{1-25}$ hydrocarbyl; and
p and r are each independently 0 or 1, and
wherein the purified 2-aryl-3-(dihydroxyfluoresceinyl)phthalimidine compound of formula (IB) has a purity of greater than 99.4%, as determined by high performance liquid chromatography.

4. The compound of claim 1, wherein the compound is a purified 2-phenyl-3-(dihydroxyfluoresceinyl)phthalimidine compound of formula (IC)

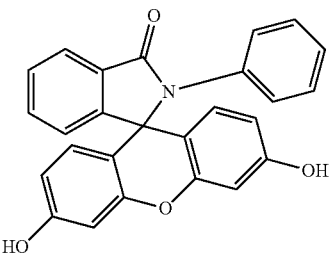

(IC)

wherein the purified 2-phenyl-3-(dihydroxyfluoresceinyl)phthalimidine compound of formula (IC) has a purity of greater than 99.4%, as determined by high performance liquid chromatography.

5. A method for the manufacture of the purified 2-hydrocarbyl-3-(dihydroxyfluoresceinyl)phthalimidine (I) compound of claim 1, the method comprising:
combining a primary amine of formula (II)

$$R\text{—}NH_2 \quad (II)$$

with an aqueous acid to provide a first reaction mixture;
adding a fluorescein compound of formula (III)

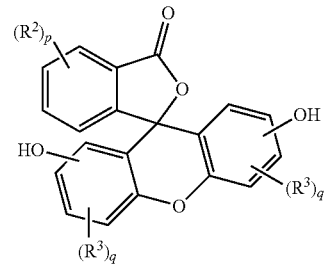

(III)

to the first reaction mixture to provide a second reaction mixture;
heating the second reaction mixture under conditions effective to provide a third reaction mixture comprising a crude phthalimidine;
combining the crude phthalimidine and an aqueous alkali solution to form an aqueous alkaline mixture;
contacting the aqueous alkaline mixture with an adsorbent to provide a semi-purified phthalimidine; and
mixing the semi-purified phthalimidine with an alcohol solution to provide the purified 2-hydrocarbyl-3-(dihydroxyfluoresceinyl)phthalimidine compound of formula (I),
wherein, in formulas (I), (II), and (III),
R is a $C_{1-25}$ hydrocarbyl;
each occurrence of $R^2$ and $R^3$ is independently a halogen or a $C_{1-25}$ hydrocarbyl;
p is 0 to 4; and
each q is independently 0 to 3.

6. The method of claim 5, further comprising one or more of
mixing the third reaction mixture with aqueous acid to provide the crude phthalimidine; or
contacting the aqueous alkaline mixture with the adsorbent, then mixing with an acid to provide the semi-purified phthalimidine.

7. The method of claim 5, further comprising
mixing the semi-purified phthalimidine with an alcohol solution and heating to form a solution comprising the semi-purified phthalimide; and
contacting the solution with an adsorbent, then mixing with deionized water to provide the purified 2-hydrocarbyl-3-(dihydroxyfluoresceinyl)phthalimidine compound of formula (I).

8. The method of claim 5, further comprising one or more of:
isolating the crude phthalimidine from the third reaction mixture, and then drying the crude phthalimidine; or
isolating the semi-purified phthalimidine, and then washing the semi-purified phthalimidine.

9. The method of claim 8, wherein the isolating of the crude phthalimidine comprises:
mixing the third reaction mixture with aqueous acid and water to provide the crude phthalimidine; and
filtering the crude phthalimidine.

10. The method of claim 8, wherein the isolating of the semi-purified phthalimidine comprises:
contacting the aqueous alkaline mixture and the adsorbent with an acid to provide the semi-purified phthalimidine; and
filtering the semi-purified phthalimidine.

11. The method of claim 5, wherein the heating of the second reaction mixture is at 100 to 200° C.

12. The method of claim 5, wherein the heating of the second reaction mixture is for 10 to 40 hours.

13. The method of claim 5, wherein the heating of the second reaction mixture is at 120 to 180° C. for 15 to 35 hours.

14. The method of claim 5, wherein the primary amine is a primary arylamine of formula (IIA)

(IIA)

wherein each occurrence of $R^1$ is independently phenyl or $C_{1-6}$ alkyl; and r is 0 or 1.

15. The method of claim 5, wherein the primary amine is aniline.

16. The method of claim 5, wherein
the aqueous acid comprises an aqueous solution of a mineral acid, and
the aqueous alkali solution comprises an aqueous solution of an alkali metal hydroxide or an alkaline earth metal hydroxide.

17. The method of claim 5, wherein
the primary amine of formula (II) is present in the second reaction mixture at a concentration of 2 to 5 molar equivalents of the fluorescein of formula (III), and
the aqueous acid is present in the first reaction mixture at a concentration of 0.8 to 1.5 molar equivalents of the primary amine of formula (II).

18. The method of claim 5, wherein
the purity of the crude phthalimidine is less than 99%,
the purity of the semi-purified phthalimidine is less than 99.5%, and
the purity of the purified 2-hydrocarbyl-3-(dihydroxyfluoresceinyl)phthalimidine compound is 99.5% or greater.

19. A method for the manufacture of a polycarbonate, the method comprising polymerizing the purified 2-hydrocarbyl-3-(dihydroxyfluoresceinyl)phthalimidine compound of claim 1 in the presence of a carbonate source under conditions effective to provide the polycarbonate.

20. The method of claim 19, wherein the polycarbonate comprises 0 to 0.8 weight percent of an impurity derived from the manufacturing of the purified 2-hydrocarbyl-3-(dihydroxyfluoresceinyl)phthalimidine compound.

* * * * *